United States Patent
Ohsaki et al.

(10) Patent No.: US 6,856,829 B2
(45) Date of Patent: Feb. 15, 2005

(54) METHOD FOR DETECTING PHYSIOLOGICAL CONDITION OF SLEEPING PATIENT BASED ON ANALYSIS OF PULSE WAVES

(75) Inventors: Rie Ohsaki, Anjo (JP); Teiyuu Kimura, Nagoya (JP); Shinji Nanba, Kariya (JP); Junichiro Hayano, 5-33 Arata-cho, Showa-ku, Nagoya-city, Aichi-pref., 466-0844 (JP); Toshiaki Shiomi, 31 Terugaoka, Meito-ku, Nagoya-city, Aichi-pref., 465-0042 (JP)

(73) Assignees: Denso Corporation, Kariya (JP); Junichiro Hayano, Aichi-ken (JP); Toshiaki Shiomi, Aichi-ken (JP)

(*) Notice: Subject to any disclaimer, the term of this patent is extended or adjusted under 35 U.S.C. 154(b) by 0 days.

(21) Appl. No.: 09/935,678

(22) Filed: Aug. 24, 2001

(65) Prior Publication Data

US 2002/0029000 A1 Mar. 7, 2002

(30) Foreign Application Priority Data

Sep. 7, 2000 (JP) .......................... 2000-271456
Nov. 17, 2000 (JP) .......................... 2000-351713

(51) Int. Cl.$^7$ .............................. A61B 5/02; A61B 6/00; A61B 5/00
(52) U.S. Cl. ....................... 600/479; 600/476; 600/481; 600/310; 600/500; 600/483; 600/484
(58) Field of Search ................................ 600/500, 501, 600/502, 503, 481, 483, 485, 490, 494, 508, 310, 476, 477, 479, 480, 484

(56) References Cited

U.S. PATENT DOCUMENTS

| | | | | |
|---|---|---|---|---|
| 4,306,567 A | * | 12/1981 | Krasner | ...................... 600/484 |
| 4,957,855 A | * | 9/1990 | MacIntyre et al. | .......... 430/551 |
| 5,101,831 A | * | 4/1992 | Koyama et al. | ............... 600/26 |
| 5,280,791 A | * | 1/1994 | Lavie | .......................... 600/509 |
| 5,540,733 A | | 7/1996 | Testerman et al. | |
| 5,810,737 A | * | 9/1998 | Dardik | .......................... 482/9 |
| 5,941,837 A | * | 8/1999 | Amano et al. | ............... 600/595 |
| 6,319,205 B1 | * | 11/2001 | Goor et al. | .................. 600/481 |
| 6,322,515 B1 | * | 11/2001 | Goor et al. | .................. 600/481 |

FOREIGN PATENT DOCUMENTS

| | | |
|---|---|---|
| JP | A-63-19161 | 1/1988 |
| JP | A-63-150047 | 6/1988 |
| JP | A-3-41926 | 2/1991 |
| JP | A-6-38965 | 2/1994 |

* cited by examiner

Primary Examiner—Max F. Hindenburg
Assistant Examiner—Navin Natnithithadha
(74) Attorney, Agent, or Firm—Posz & Bethards, PLC

(57) ABSTRACT

A physiological condition detecting method detects pulse waves from the body of a patient, and creates the envelope of the pulse waves by connecting every peak of the pulse waves. It determines that the patient is in non-REM sleep, if the envelope fluctuates regularly. It determines that the patient is in REM sleep, if the envelope fluctuates irregularly. Further the method calculates and normalizes the amplitude and period of the envelope. It determines whether the patient has obstructive sleep apnea syndrome based on the normalized amplitude. It determines whether the patient has central sleep apnea syndrome based on the normalized period. It determines that the patient has mixed sleep apnea syndrome based on the normalized amplitude and the normalized period.

34 Claims, 14 Drawing Sheets

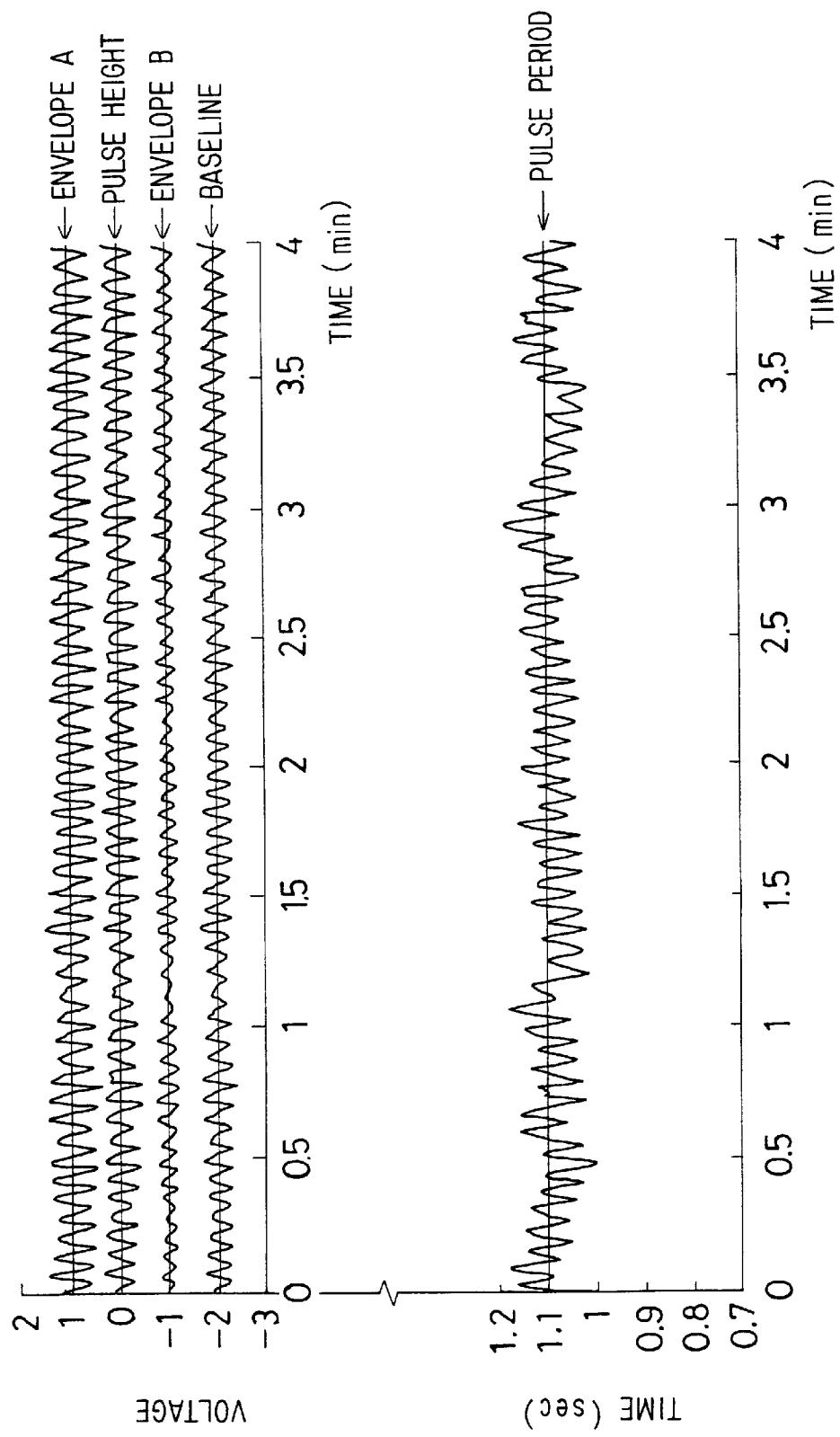

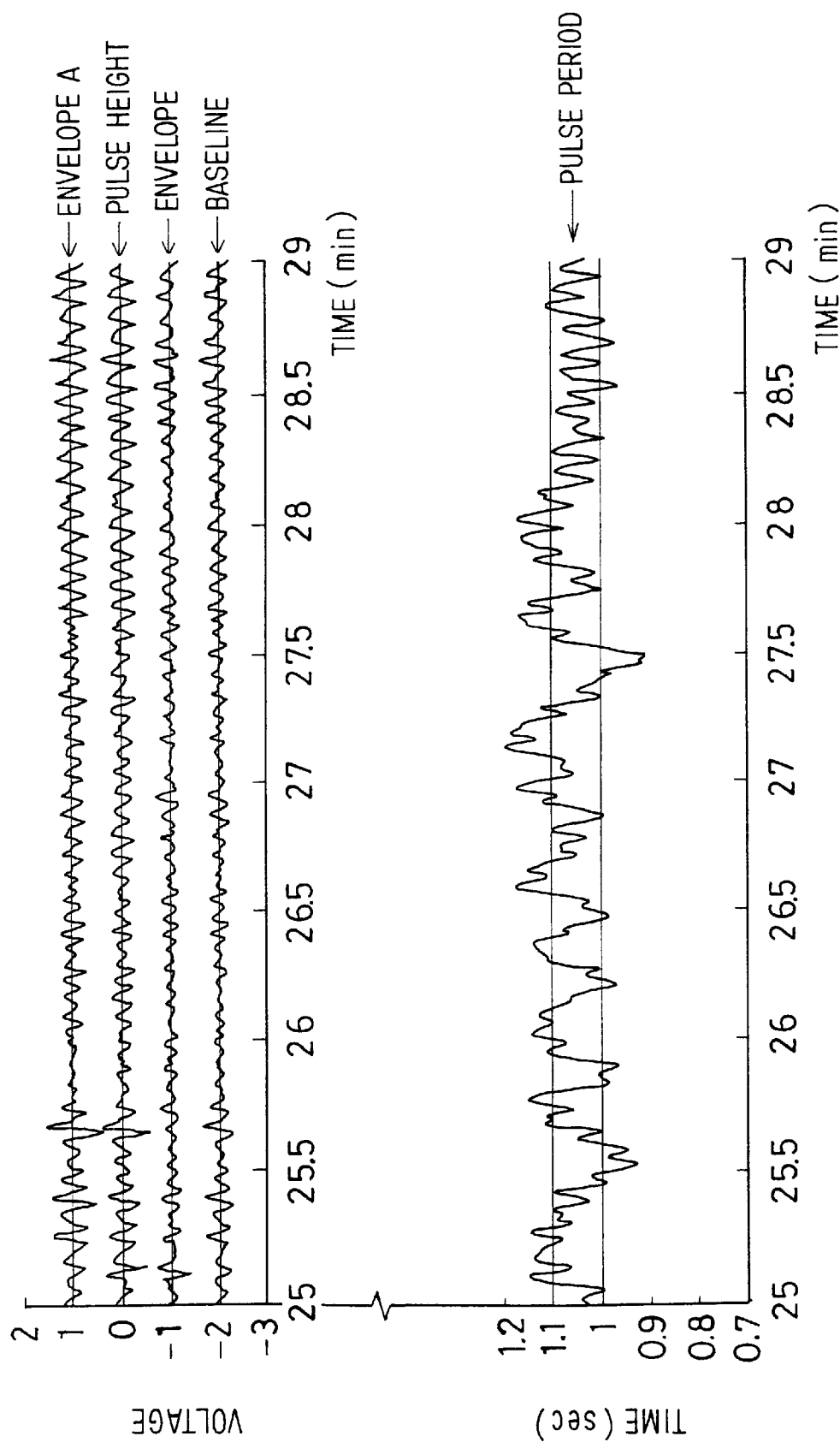

EUPNEA

OSA

CSA

EUPNEA

OSA

CSA

METHOD FOR DETECTING PHYSIOLOGICAL CONDITION OF SLEEPING PATIENT BASED ON ANALYSIS OF PULSE WAVES

CROSS REFERENCE TO RELATED APPLICATION

This application is based on and incorporates herein by reference Japanese Patent Applications No. 2000-271456 filed on Sep. 7, 2000 and NO. 2000-351713 filed on Nov. 17, 2000.

BACKGROUND OF THE INVENTION

1. Field of the Invention

The present invention relates to a method for detecting the physiological condition of a sleeping patient.

2. Related Art

The sleep condition (depth of a sleep) of a patient is usually detected from a polysomnogram which shows signals which are simultaneously measured on the patient's body by a polysomnographer. The polysomnogram includes an electroencephalogram, an oclogram, an electromyogramn, an electrocardiogram and the like. The patient needs to be hospitalized for such measurement, because the polysomnographer is a large-scaled facility. Further, the patient feels uncomfortable during the measurement, because sensors are attached on his/her head and face. Accordingly, the patient's sleep is disturbed and, as a result, accurate data is not obtained.

JP-A-3-41926 discloses an alternative method for detecting a sleep condition of a patient. The method detects a respiration rate and a pulse rate of the patient, and determines the patient's sleep condition based on the detected respiration rate and pulse rate as follows. The Pulse period, which corresponds to the R-R period in the electrocardiogram, is calculated, and thereafter the sleep condition (REM sleep or non-REM sleep) is detected from the fluctuation of the pulse period. In order to obtain the pulse period, the peak (top or bottom) of every pulse wave should be accurately detected. When pulse waves fluctuate regularly, the peaks of the pulse waves can be detected accurately. However, pulse waves may fluctuate irregularly if the patient moves his/her body during sleep. In this case, the peaks of pulse waves may shift due to a factor other than the fluctuation of blood flow and consequently may be incorrectly detected. In order to obtain the pulse period based on the peaks of the pulse waves which may be provided as the result of the misdetection, complicated calculations are required. Accordingly, this method cannot readily detect the patient's sleep condition.

Further, the pulse period varies distinctly depending on whether the patient is in the REM sleep or non-REM sleep, only when the patient is healthy. When the patient is ill or old, the pulse period varies only slightly depending on whether the patient is in the REM sleep or non-REM sleep. Accordingly it is difficult to detect the sleep condition.

The diagnosis of sleep apnea syndrome is also made by examining all the signals in the polysomnogram. Therefore it is expensive and requires time and effort for a patient to have examination for sleep apnea syndrome, because the patient needs to be hospitalized. As a result, it is difficult to detect and treat the sleep apnea syndrome early.

SUMMARY OF THE INVENTION

The present invention has an object to provide a method for accurately detecting the sleep condition of a patient at home without executing complicated calculation and without being affected by noise due to the movement of the patient's body.

The present invention also has an object to provide a method for diagnosing sleep apnea syndrome (SAS) at home without imposing a burden on a patient.

A first method according to the present invention detects the sleep condition of a patient by analyzing the pulse waves of the patient. The first method measures pulse waves on the patient's body, and creates the envelope of the pulse waves by connecting the tops and bottoms of the pulse waves. The first method determines that the patient is in non-REM sleep, if the created envelope fluctuates regularly. It determines that the patient is in REM sleep, if the created envelope fluctuates irregularly.

The pulse height, which is a height of every pulse wave, or the baseline, which is a line connecting a middle point of every pulse wave, may be created instead of the envelope of the pulse waves. In this case, it is determined that the patient is in non-REM sleep, if the created pulse height or baseline fluctuates regularly. It is determined that the patient is in REM sleep, if the created pulse height or baseline fluctuates irregularly.

A second method according to the present invention diagnoses a patient as SAS by analyzing the pulse waves of the patient. The second method measures pulse waves on the patient's body, and analyzes the pulse wave data. Based on the result of the analysis, the second method determines whether the patient has SAS. Preferably, the type of the SAS is also determined based on the result of the analysis, if it is determined that the patient has SAS.

BRIEF DESCRIPTION OF THE DRAWINGS

The above and other objects, features and advantages of the present invention will become more apparent from the following detailed description made with reference to the accompanying drawings. In the drawings

FIG. 5 is a graph of the envelopes, pulse height and baseline of pulse waves while pulse period fluctuates regularly;

FIG. 6 is a graph of the envelopes, pulse height and baseline of pulse waves while pulse period fluctuates irregularly;

DETAILED DESCRIPTION OF THE PREFERRED EMBODIMENT (First Embodiment)

Figure 1:
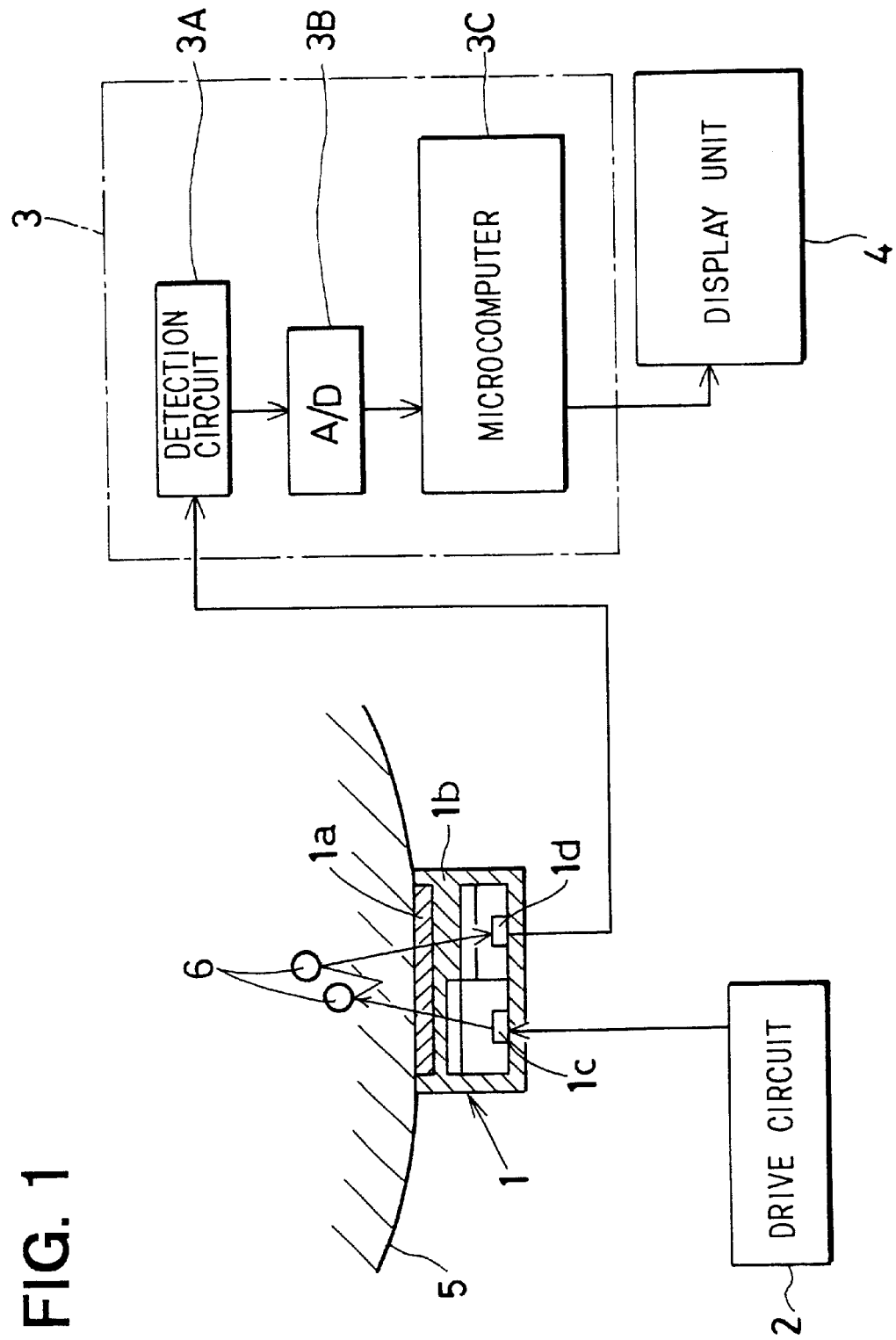
FIG. 1 is a schematic diagram of an apparatus for detecting the physiological condition of a patient.

A method according to a first embodiment detects the sleep condition of a patient by a physiological condition detection apparatus shown in FIG. 1. The physiological condition detection apparatus includes a pulse wave sensor 1, a drive circuit 2, a data processing unit 3 and a display unit 4. The data processing unit 3 includes a detection circuit 3A, an A/D converter 3B, and a microcomputer 3C. The pulse wave sensor 1 is a well-known optical sensor, and worn on the patient's wrist 5 or finger. The sensor 1 includes a sensor housing 1b on which a window 1a is formed. The sensor 1 further includes a light emitting element 1c and a light receiving element 1d in the housing 1b. The drive circuit 2 drives the light emitting element 1c to emit light toward the patient's wrist 5. A portion of the emitted light penetrates the capillary arteriole 6 in the inside of the patient's wrist 5 and is absorbed by the hemoglobin in the blood. The rest of the emitted light is reflected and scattered by the capillary arteriole 6, and partly reaches the light receiving element 1d. As the amount of the hemoglobin in the blood fluctuates in waves due to the pulsation of the patient's blood, the amount of the light absorbed by the hemoglobin also fluctuates in waves. As a result, the amount of the light which is reflected by the capillary arteriole 6 and reaches the light receiving element 1d fluctuates in waves. This fluctuation in the amount of the light received by the light receiving element 1d is detected as pulse wave information. The pulse wave sensor 1 further converts the pulse wave information into electrical signals (i.e., voltage signals), and outputs the electrical signals to the data processing unit 3.

In the data processing unit 3, the detection circuit 3A receives and amplifies the electrical signals. The A/D converter 3B converts the amplified analog signals to digital signals at a sampling frequency of 100 Hz. The digital signals are outputted to the microcomputer 3C. The microcomputer 3C is programmed to detect the sleep condition of the patient by using the digital signals which represent pulse wave information detected from the sleeping patient as follows.

Figure 2:
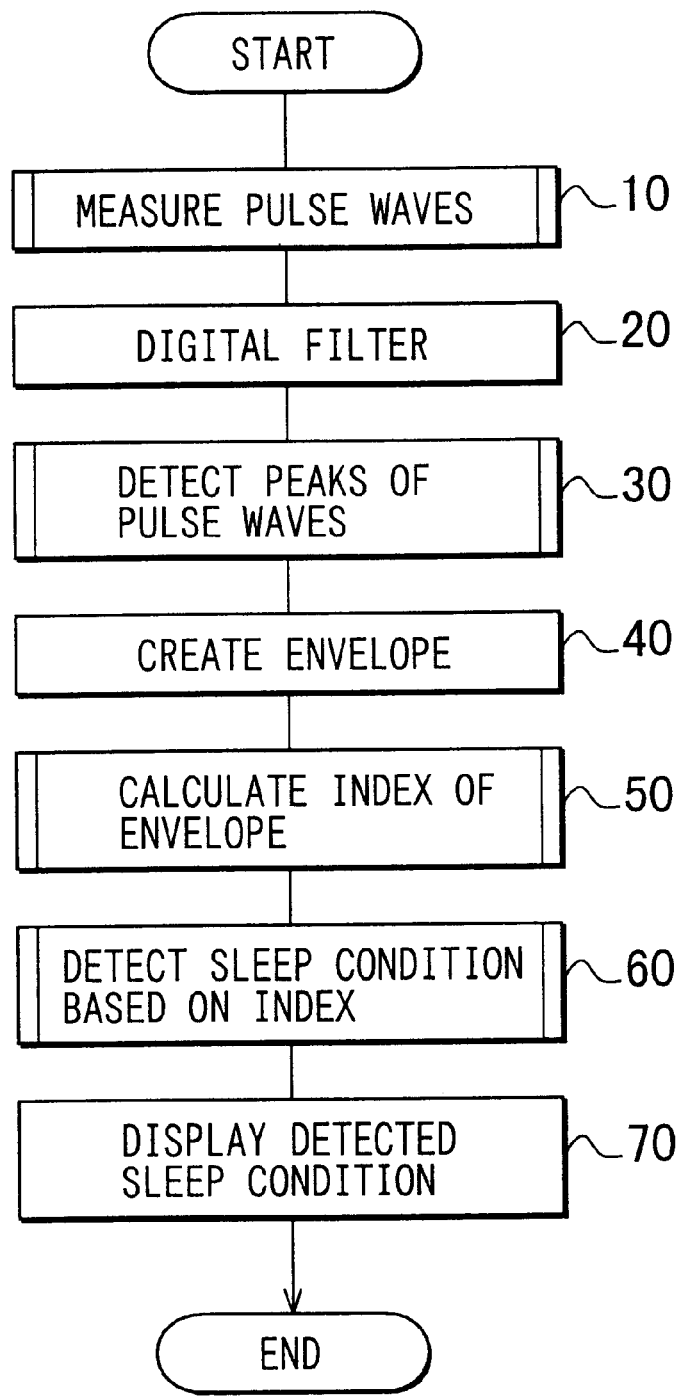
FIG. 2 is a flowchart of a process for detecting the sleep condition of a patient according to a first embodiment.

Referring to FIG. 2, pulse wave data is measured from the digital signals at step 10. The pulse wave data is filtered through a digital filter so that unwanted frequency component of the pulse waves are eliminated at step 20. The peak of every pulse wave is detected from the pulse wave data at step 30.

Figure 3:
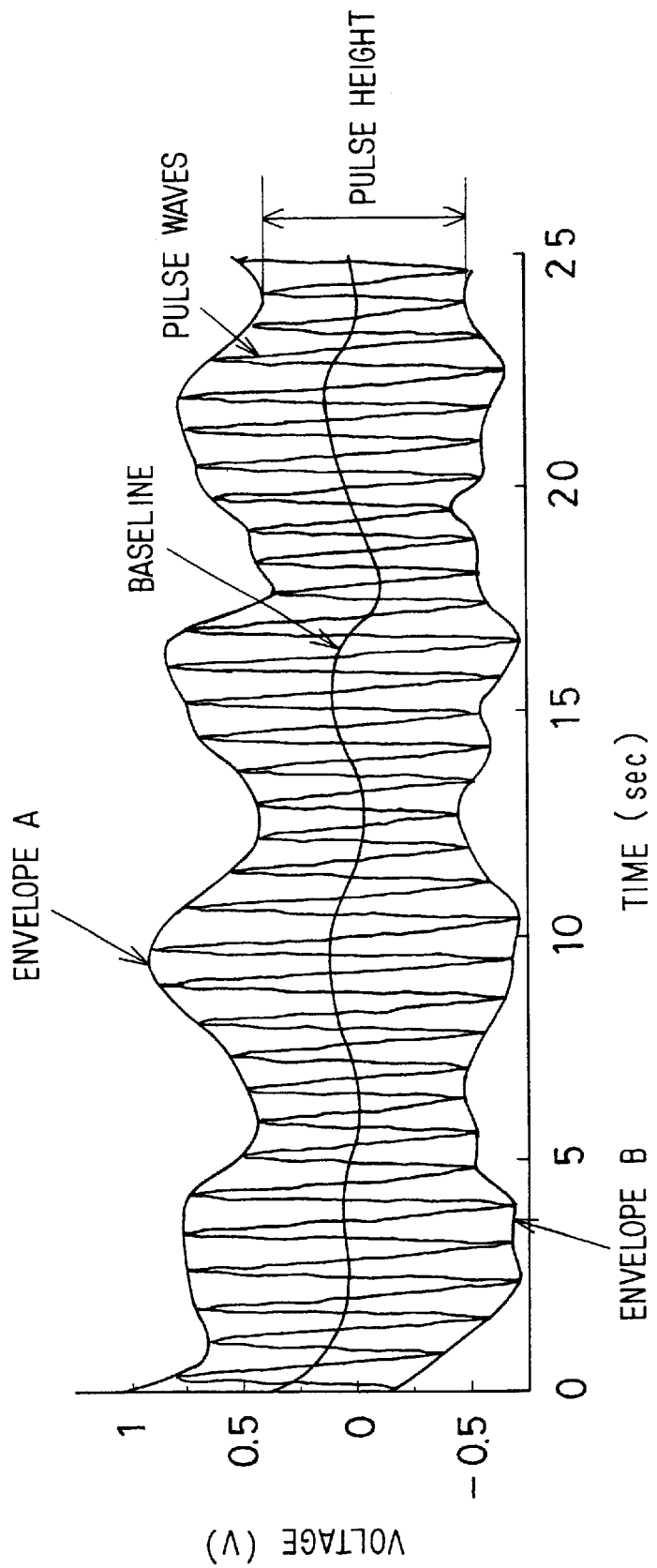
FIG. 3 is a graph of pulse waves detected from a patient.
Figure 4A:
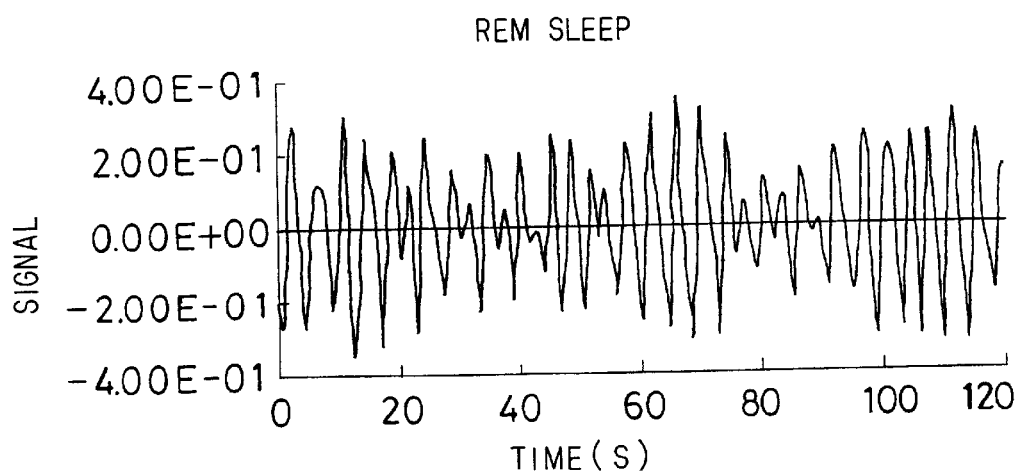
FIGS. 4A and 4B are graphs of envelopes of pulse waves detected from the patient in REM sleep and in non-REM sleep, respectively.
Figure 4B:
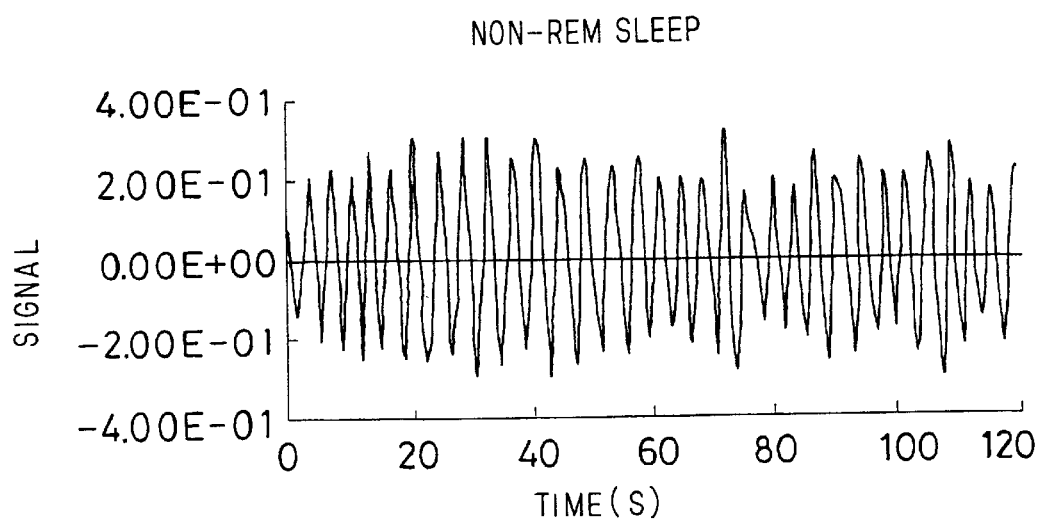

One of the envelopes of the pulse waves is created at step 40. FIG. 3 shows pulse waves detected from the patient. Two envelopes A, B can be created by connecting the peaks of the pulse waves as shown in FIG. 3. One envelope A is obtained by connecting the tops of the pulse waves, while the other envelope B is obtained by connecting the bottoms of the pulse waves. Either of the envelopes A, B may be created at step 40. FIGS. 4A and 4B show the envelopes of the pulse waves detected during the patient's REM sleep and non-REM sleep, respectively.

At step 50, the characteristics of the envelope A, B is detected at regular intervals as follows. A statistical index such as the average, maximum value, minimum value, variance, deviation or the like is employed for representing the characteristics of the envelope A, B over an interval. The employed index is calculated over and at regular intervals (i.e., 20 seconds) at step 50. At step 60, the sleep condition of the patient is detected based on the fluctuation of the calculated index. As shown in FIG. 5, the envelopes A, B fluctuate regularly while the pulse period fluctuates regularly. As shown in FIG. 6, the envelopes A, B fluctuate irregularly while the pulse period fluctuates irregularly. It is known that the patient is in non-REM sleep if the pulse period fluctuates regularly. It is also known that the patient is in REM sleep if the pulse period fluctuates irregularly.

Further, the envelopes A, B of the pulse waves actually fluctuate more irregularly during the patient's REM sleep than during the patient's non-REM sleep as shown in FIGS. 4A and 4B. In the case of non-REM sleep, the standard deviations calculated from the envelope data shown in FIG. 4B over intervals of 20 seconds are 0.15 (0–20 s), 0.16 (20–40 s) and 0.16 (40–60 s). That is, the standard deviations do not vary largely. In contrast to this, in the case of REM sleep, the standard deviations calculated from the envelope data shown in FIG. 4A over intervals of 20 seconds are 0.16 (0–20 s), 0.09 (20–40 s), 0.10 (40–60 s) and 0.15 (60–80 s) That is, the standard deviations vary largely Therefore, it may be determined that the patient is in non-REM steep, if the envelope A, B fluctuates regularly, that is, the statistical index varies within the predetermined range. Further, it may be determined that the patient is in REM sleep, if the envelope A, B fluctuates irregularly, that is, the statistical index varies exceeding the predetermined range.

Accordingly, it is determined at step 60 that the patient is in REM sleep, if the variation of the index is within 25%. Further it is determined at step 60 that the patient is in non-REM sleep, if the variation of the index is over 25%. The detected sleep condition is displayed by the display unit 4 at step 70.

(Second Embodiment)

A method according to a second embodiment diagnoses a patient as sleep apnea syndrome (SAS) by a physiological condition detection apparatus (shown in FIG. 1) which has the similar configuration as the first embodiment. Further the method determines the type of SAS. The type of SAS is obstructive sleep apnea syndrome (OSAS), central sleep apnea syndrome (CSAS), or mixed sleep apnea syndrome (MSAS). In obstructive sleep apnoeaic (OSA) condition, the breathing movement of the patient's thoracic part and abdominal wall is maintained, but ventilation through the patient's mouth or nose is stopped due to partially obstructed upper airway. In central sleep apnoeaic (CSA) condition, movement of the patient's respiratory muscle is stopped due to a standstill of respiratory center or a disturbance of excitation-conduction. The patient is diagnosed as MSAS if he/she shifts from CSA condition to OSA condition.

In the physiological condition detection apparatus, similarly to the first embodiment, a pulse sensor 1 is driven by a drive circuit 2 and detects pulse wave information from the patient's body. The pulse sensor 1 outputs the pulse wave information as electrical signals to a data processing unit 3. In the data processing unit 3, a detection circuit 3A and an A/D converter 3B operates similarly to the first embodiment, and a microcomputer 3C receives digital signals from the A/D converter 3B. The microcomputer 3C is programmed to diagnose the patient as SAS by using the digital signals which represents the pulse wave information detected from the sleeping patient as follows.

Figure 7:
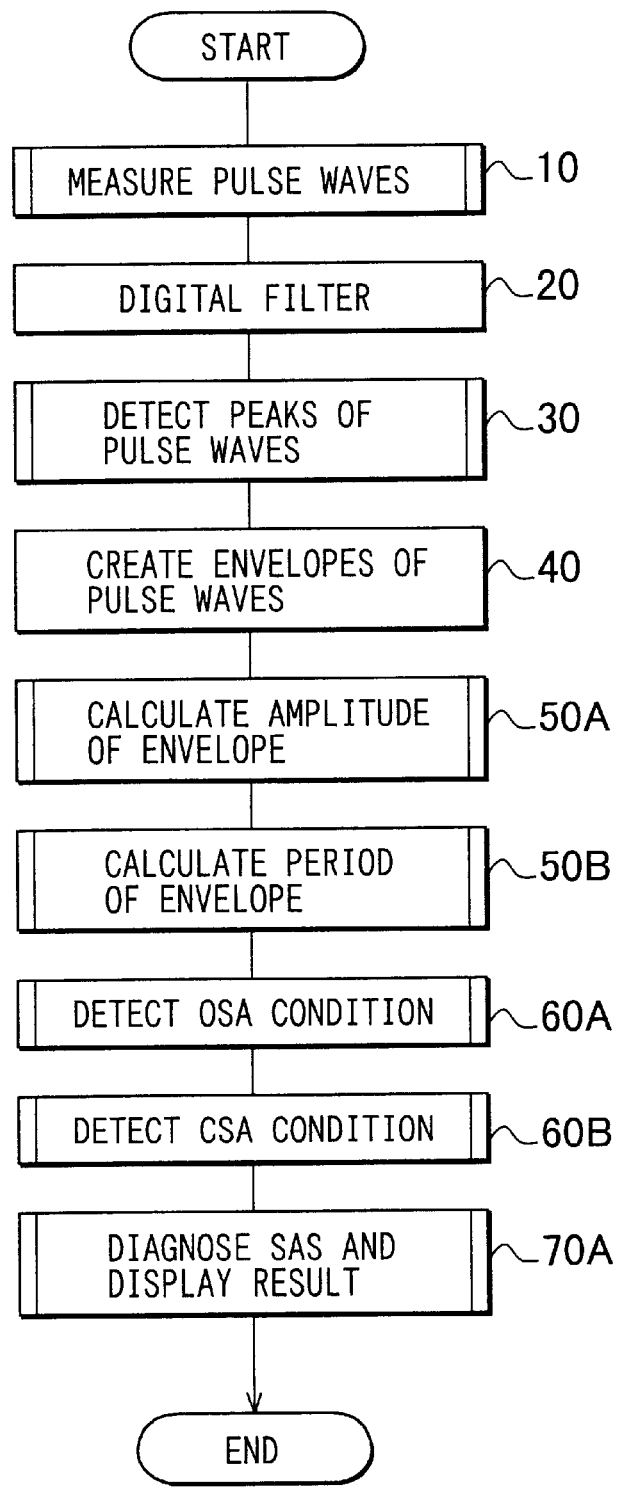
FIG. 7 is a flowchart of a process for diagnosing sleep apnea syndrome according to a second embodiment.

Referring to FIG. 7, the received digital signals are processed at steps 10–30 and one of the envelopes A, B of the pulse waves is created at step 40 similarly to the first embodiment. However, both of the envelopes A, B may be created at step 40, if necessary at later steps.

Figure 8:
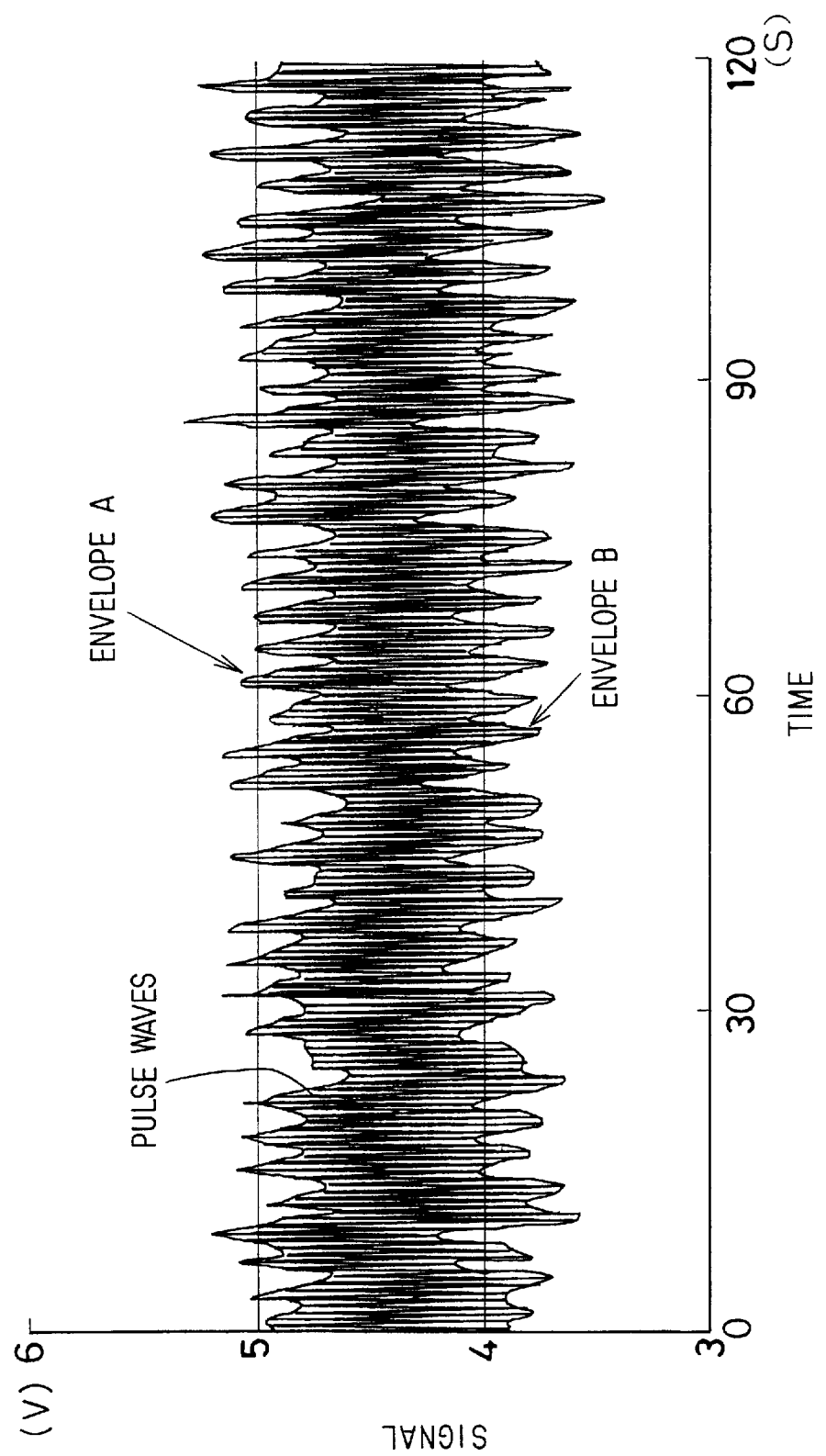
FIG. 8 is a graph of pulse waves detected from a patient in eupneic condition.
Figure 9:
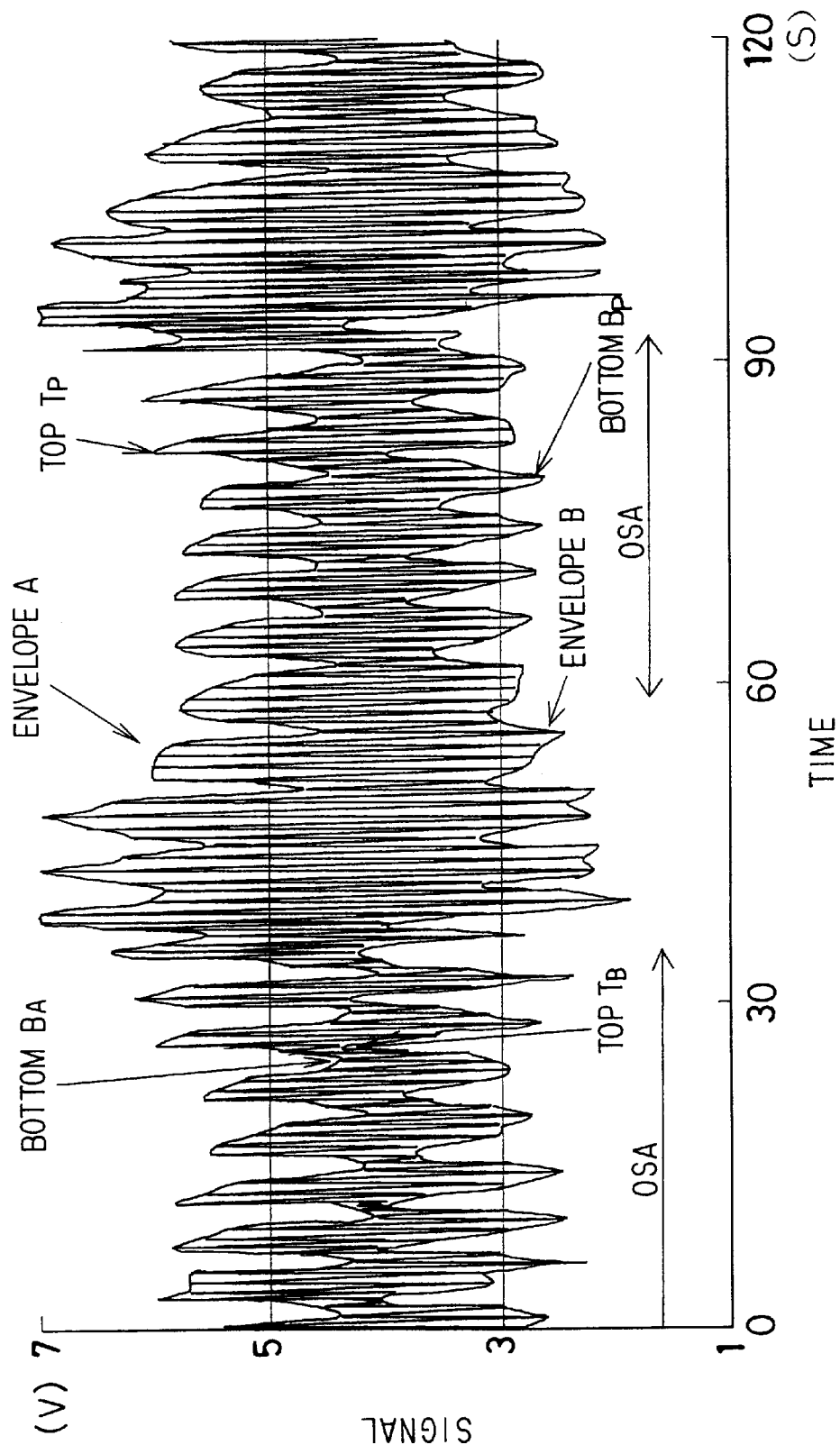
FIG. 9 is a graph of pulse waves detected from a patient in obstructive sleep apnoeaic condition.

FIG. 8 shows pulse waves detected from the patient in eupneic condition, and FIG. 9 shows pulse waves detected from the patient in OSA condition. The envelopes A, B shown in FIG. 9 fluctuate largely as compared with the envelopes A, B shown in FIG. 8. Specifically, the normalized amplitude of the envelope A, B (FIG. 9) in OSA condition is twice the normalized amplitude of the envelope A, B (FIG. 8) in eupneic condition or higher. Accordingly the amplitude of the envelope A, B is calculated at step 50A for detecting OSA condition. The calculated amplitude is normalized with respect to the amplitude of the pulse wave, because the amplitude of the envelope changes in proportion to the amplitude of the pulse wave. For example, the amplitude of the envelope is normalized by being divided by the amplitude of the pulse wave averaged over one period of the pulse waves.

Figure 10:
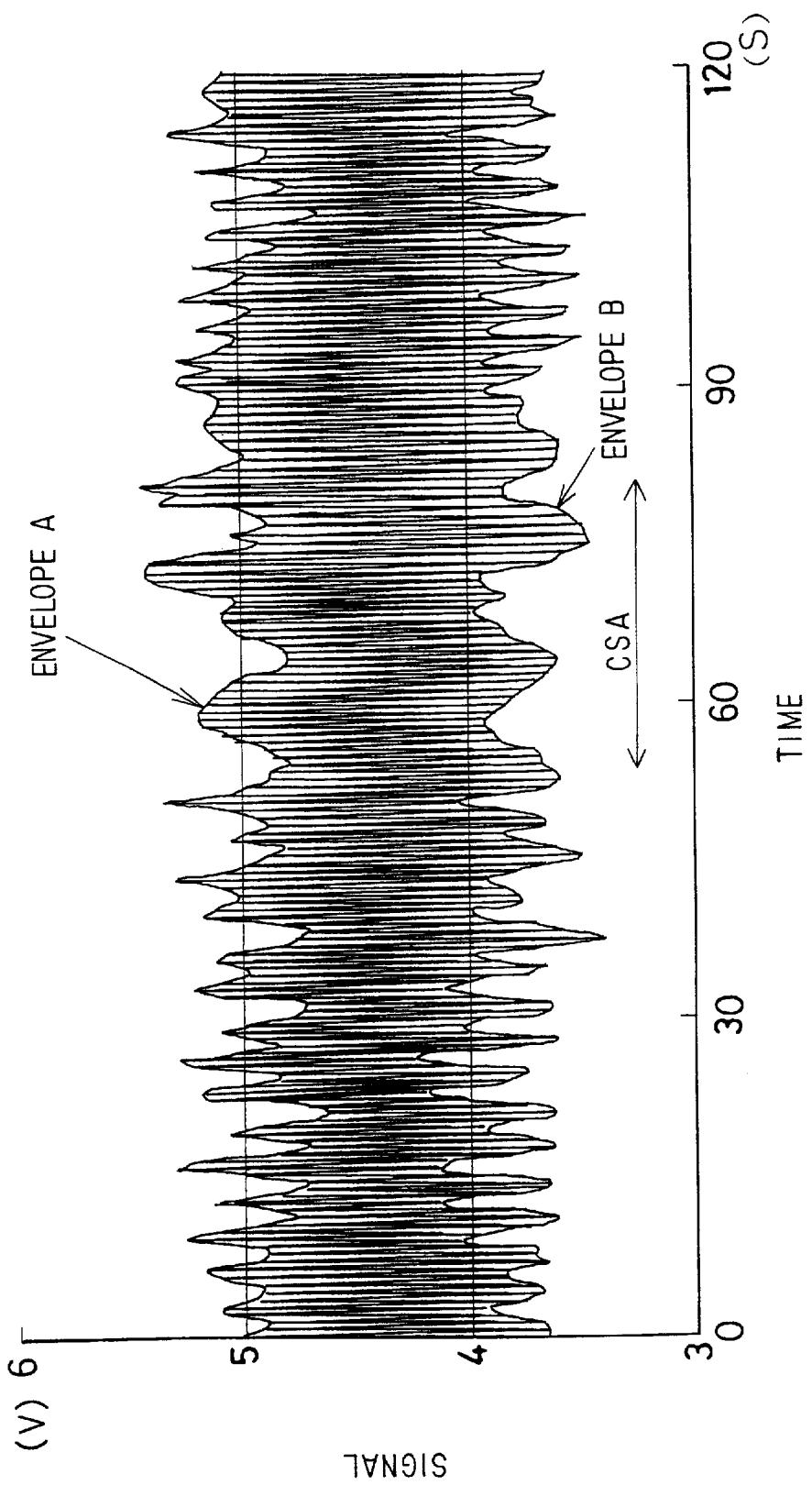
FIG. 10 is a graph of pulse waves detected from a patient in central sleep apnoeaic condition.

FIG. 10 shows pulse waves detected from the patient in CSA condition. In CSA condition, movement of the patient's thoracic part is stopped. Therefore pulse wave data detected from the patient in CSA condition does not include signals which represent respiration. Accordingly, the envelope A, B fluctuates in a long period as shown in FIG. 10. Specifically, it fluctuates in a period of roughly 10 seconds (7–12 seconds). In contrast to this, the envelope A, B in eupneic condition or OSA condition does not fluctuate in a long period as shown in FIG. 8 or 9. Therefore the period of the fluctuation of the envelope A, B is calculated at step 50B for detecting CSA condition. The calculated period is also normalized.

At step 60A, it is determined that the patient is in OSA condition if the normalized amplitude of the envelope A, B is twice that in the eupnea condition or higher. At step 60B, it is determined that the patient is in CSA condition if the normalized period is equal to or longer than 7 seconds.

At step 70A, a diagnosis of SAS is made based on the results of steps 60A and 60B. Further the type of SAS is determined based on the results of steps 60A and 60B, if the patient is diagnosed as SAS. The patient is diagnosed as MSAS, if he/she shifts from CSA condition to OSA condition. The result of the diagnosis is displayed by the display unit 4.

(Modifications)

Figure 11:
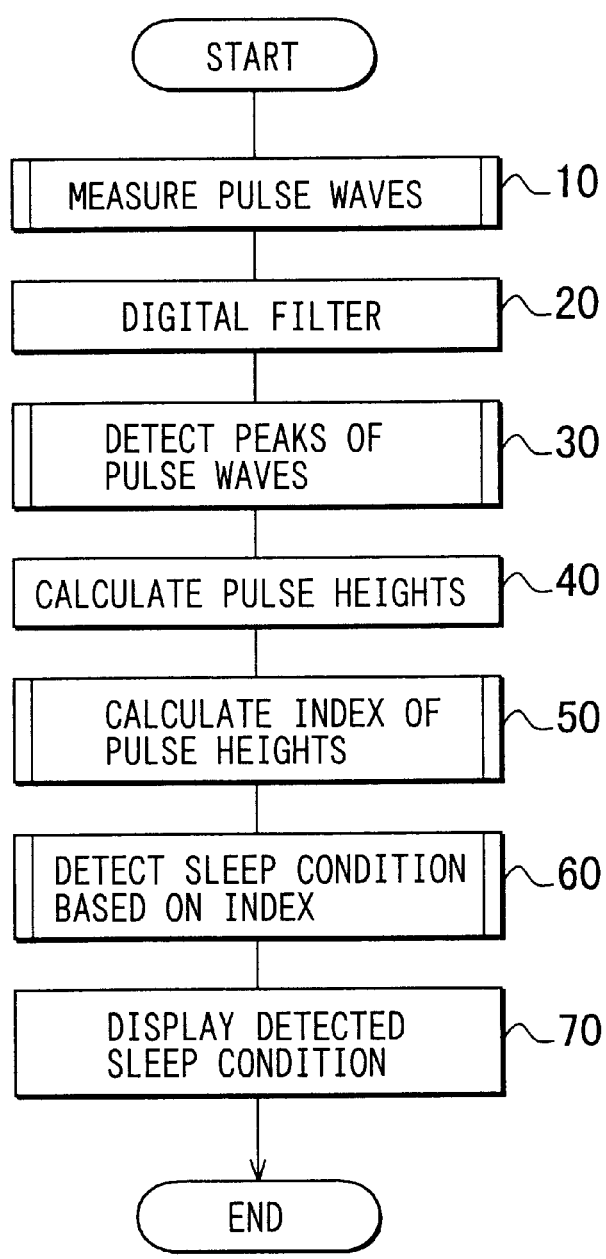
FIG. 11 is a flowchart of a process for detecting the sleep condition of a patient according to a modification of the first embodiment.

In the first embodiment, the sleep condition of the patient may be detected based on the pulse height of the pulse waves as shown in FIG. 11. The pulse height is defined as the height of a pulse wave as shown in FIG. 3. The pulse height of every pulse wave is created instead of the envelope A, B at step 40. Further statistical index which represents the characteristics of pulse height is calculated over and at regular intervals at step 50. As shown in FIG. 4, the pulse height fluctuates regularly while the pulse period fluctuates regularly. As shown in FIG. 5, the pulse height fluctuates irregularly while the pulse period fluctuates irregularly. Accordingly, it may be determined at step 60 that the patient is in non-REM sleep, if the calculated index varies within a predetermined range. Further it may be determined at step 60 that the patient is in REM sleep, if the calculated index varies exceeding the predetermined range.

Figure 12:
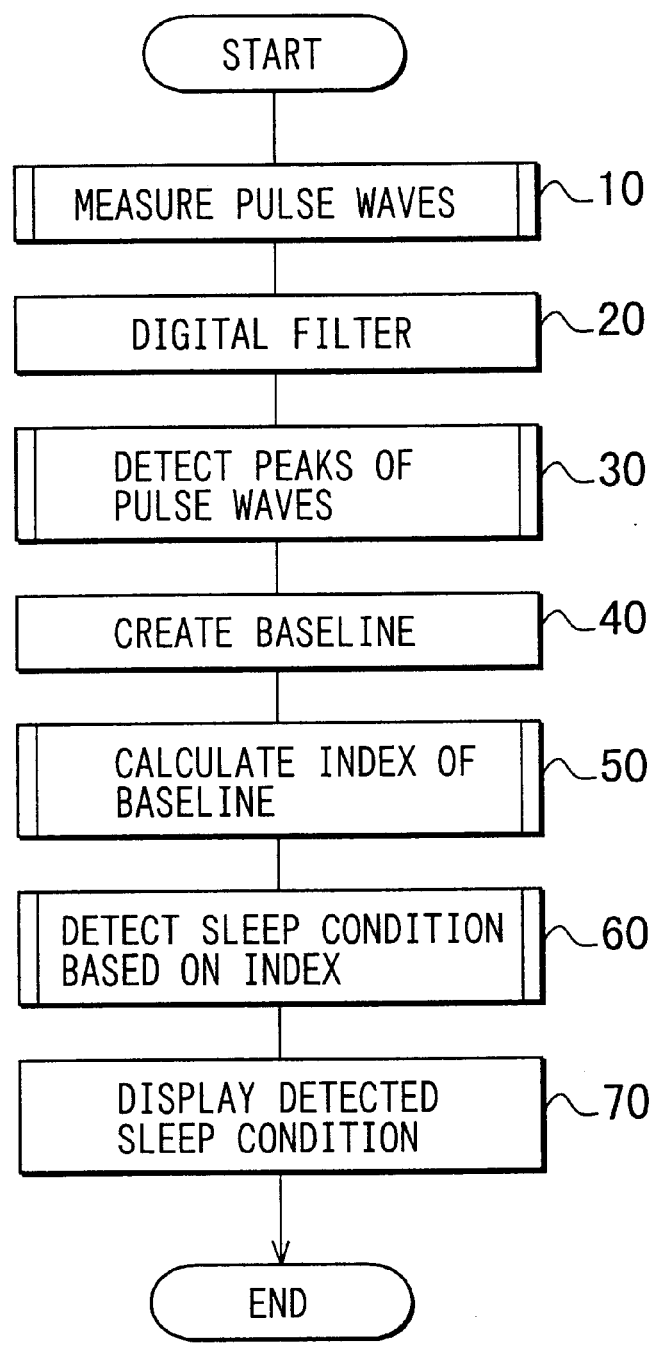
FIG. 12 is a flowchart of a process for detecting the sleep condition of a patient according to another modification of the first embodiment.

Further in the first embodiment, the sleep condition of the patient may be detected based on the baseline of the pulse waves as shown in FIG. 12. The baseline is a line which connects the middle point of the pulse height of every pulse wave as shown in FIG. 3. The baseline of the pulse waves is created instead of the envelope A, B at step 40. Further statistical index which represents the characteristics of baseline is calculated over and at regular intervals at step 50. As shown in FIG. 5, the baseline fluctuates regularly while the pulse period fluctuates regularly. As shown in FIG. 6, the baseline fluctuates irregularly while the pulse period fluctuates irregularly. Accordingly, it may be determined at step 60 that the patient is in non-REM sleep, if the calculated index varies within a predetermined range. Further it may be determined at step 60 that the patient is in REM sleep, if the calculated index varies exceeding the predetermined range.

In the second embodiment, another attribute of the envelope A, B of the pulse waves may be calculated instead of the amplitude of the envelope A, B. That is, another attribute of the envelope A, B may be employed for detecting OSA condition. When the patient is in OSA condition, a bottom $B_A$ of the envelope A is very close to a top $T_B$ of the envelope B as shown in FIG. 8. In contrast to this, a bottom $B_A$ of envelope A and a top $T_B$ of the envelope B is not close when the patient is in eupneic condition. Accordingly, the closeness of the bottom $B_A$ of the envelope A and the top $T_B$ of the envelope B may be calculated and normalized at step 50A. In this case, at step 60A, it is determined whether the patient is in OSA condition based on the normalized closeness of the bottom $B_A$ of the envelope A and the top $T_B$ of the envelope B.

Furthermore an attribute of the pulse waves may be employed for detecting OSA condition. When the patient is in OSA condition, the tops $T_P$ and bottoms $B_P$ of the pulse waves fluctuate largely as shown in FIG. 9. Therefore the degree of the fluctuation of the tops $T_P$ and bottoms $B_P$ may be calculated and normalized at step 50A, and it is determined at step 60A whether the patient is in OSA condition based on the normalized degree of the fluctuation of the tops $T_P$ and bottoms $B_P$ of the pulse waves. In this case, the envelope A, B is not used at step 50A, because the tops $T_P$ and bottoms $B_P$ of the pulse waves can be obtained without the envelope A, B of the pulse waves.

Figure 13A:
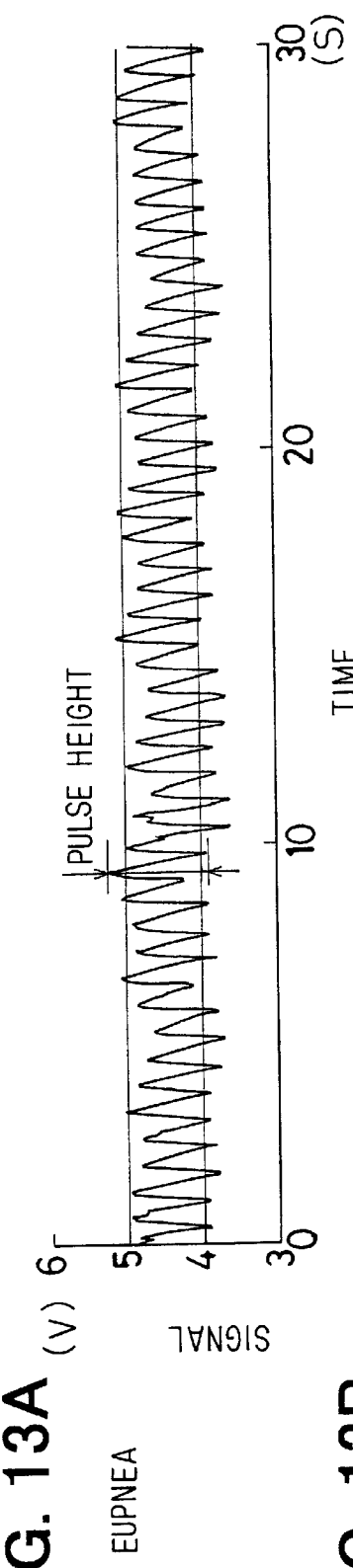
FIGS. 13A–13C are graphs of pulse waves detected from the patient in eupneic condition, the patient in obstructive sleep apnoeaic condition, and the patient in central sleep apnoeaic condition (enlargements of FIGS. 8, 9, and 10) respectively.
Figure 13B:
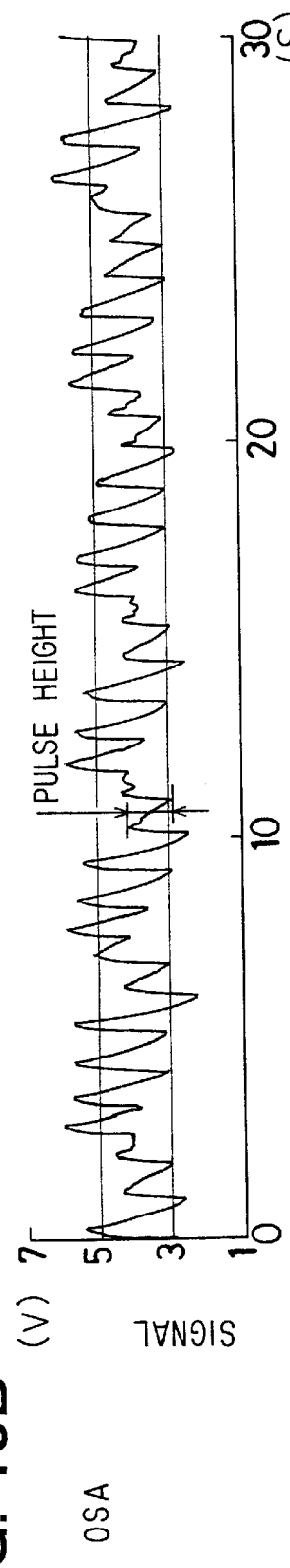
Figure 13C:
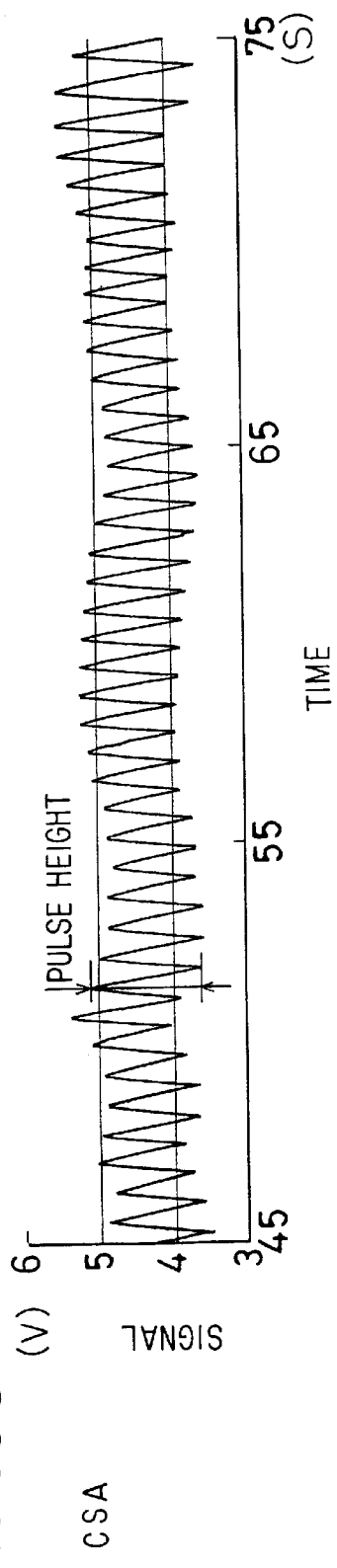

Moreover OSA condition may be detected based on the degree of the fluctuation of the pulse height of the pulse. FIGS. 13A–13C show pulse waves obtained by enlarging FIGS. 8, 9 and 10 with respect to the horizontal axis (time axis), respectively. The pulse height of the pulse waves detected from the patient in eupneic condition or CSA condition does not fluctuate largely. Specifically, the pulse height of the pulse waves fluctuate within a range of 20%. In contrast to this, when the patient is in OSA condition, the pulse height of the pulse waves fluctuates largely. Specifically, the minimum pulse height of the pulse waves is equal to or lower than 50% of the maximum pulse height of the pulse waves. Accordingly, the pulse height of every pulse wave may be calculated at step 50A. Further a ratio of the minimum pulse height to the maximum pulse height is calculated at step 50A. At step 60A, it is determined that the patient is in OSA condition if the ratio is equal to or lower than 50%.

Figure 14A:
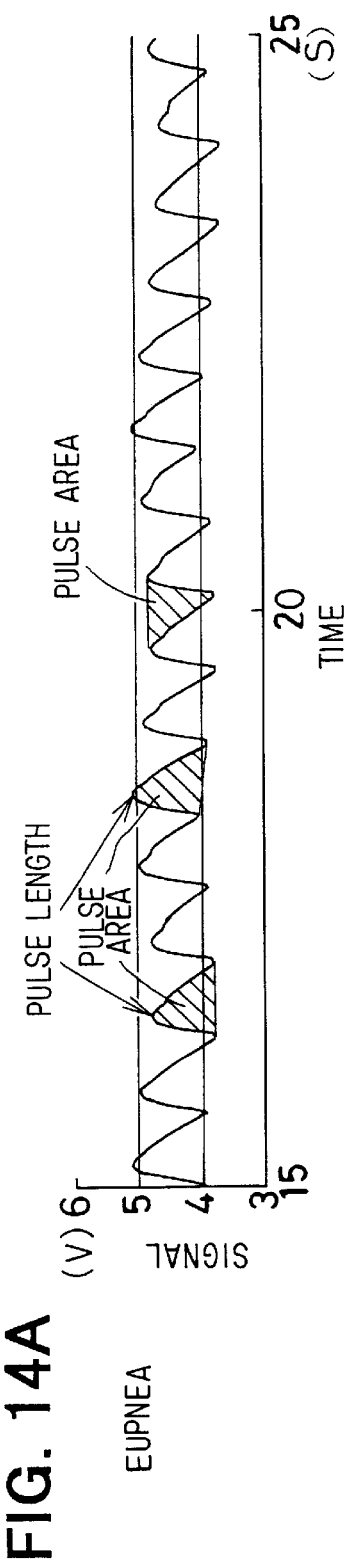
FIGS. 14A–14C are graphs of pulse waves detected from the patient in eupneic condition, the patient in obstructive sleep apnoeaic condition, and the patient in central sleep apnoeaic condition (enlargements of FIGS. 13A–13C) respectively.
Figure 14B:
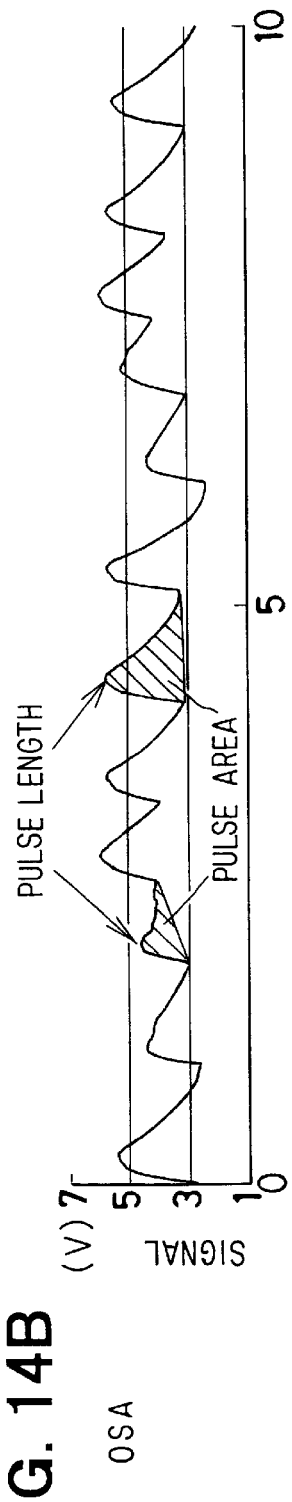
Figure 14C:
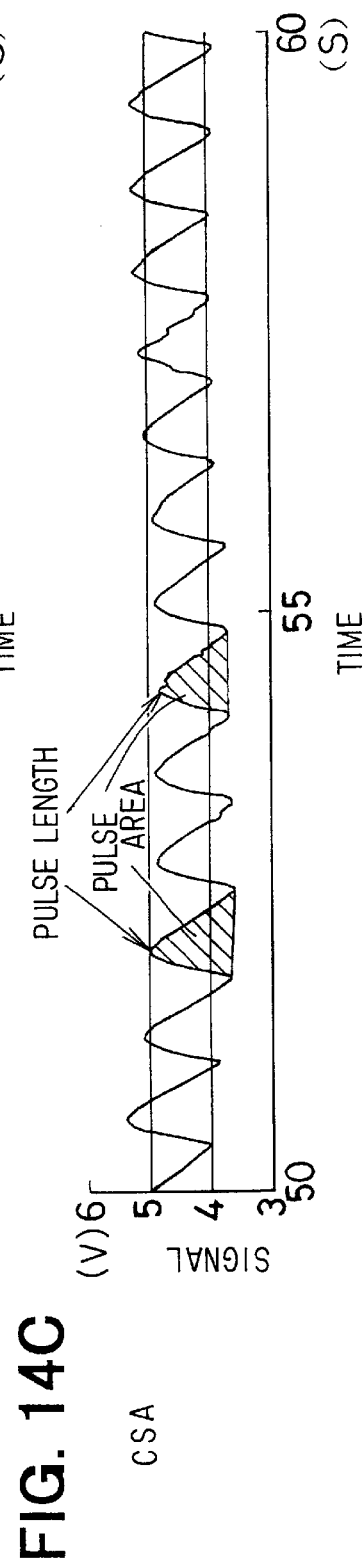

Further the areas or lengths of the pulse waves may be employed for detecting OSA condition. FIGS. 14A–14C show pulse waves obtained by enlarging FIGS. 13A–13C with respect to the horizontal axis (time axis), respectively. The area of a pulse wave (pulse wave area) means the area formed by the pulse wave between two bottoms and the line which connects the bottoms or formed by the pulse wave between two tops and the line which connects the tops as shown in FIGS. 14A–14C. The length of a pulse wave (pulse wave length) means the length of the pulse wave between two bottoms or two tops as shown in FIGS. 14A–14C.

The pulse wave areas of the pulse waves detected from the patient in eupneic condition or in CSA condition do not vary largely as shown in FIG. 14A or 14C. Specifically, the pulse wave areas vary within a range of 20%. In contrast to this, the pulse wave areas of the pulse waves detected from the patient in OSA condition vary largely. Specifically, the minimum pulse wave area is equal to or less than 50% of the maximum pulse wave area. Accordingly, the pulse wave area of every pulse wave may be calculated at step 50A. Further the ratio of the minimum pulse wave area to the maximum pulse wave area is calculated at step 50A. It is determined at step 60A that the patient is in OSA condition, if the ratio is equal to or less than 50%.

On the other hand, the pulse wave lengths of the pulse waves detected from the patient in eupneic condition or in CSA condition do not vary largely as shown in FIG. 14A or 14C. Specifically, the pulse wave lengths vary within a range of 10%. In contrast to this, the pulse wave lengths of the pulse waves detected from the patient in OSA condition vary largely. Specifically, the minimum pulse wave length is equal to or less than 75% of the maximum pulse wave length. Accordingly, the pulse wave length of every pulse wave may be calculated at step 50A. Further the ratio of the minimum pulse wave length to the maximum pulse wave length is calculated at step 50A. It is determined at step 60A that the patient is in OSA condition, if the ratio is equal to or less than 75%.

Further OSA condition may be detected based on the difference between the fluctuation of the pulse waves and fluctuation of pulse waves detected from the patient in eupneic condition.

In the above embodiments and modifications, the pulse wave sensor 1 may be an ultrasonic sensor, a Doppler sensor or a pressure type sensor.

The effects of the above embodiments and modifications are as follows. In the first embodiment and its modifications, the methods detect the sleep condition of the patient without executing complicated calculations, because the regularities of the fluctuation of the envelope, the pulse height or the baseline is not significantly affected by the inaccuracy of the detected tops or bottoms of the pulse waves. In this way, the methods detect the sleep condition of the patient more simply.

Further in the first embodiment and its modifications, pulse wave information does not need to be obtained very accurately with respect to time. Therefore the methods can detect the sleep condition of the patient without being significantly affected by disturbance.

In the second embodiment and its modifications, the patient can readily have examination at home, because a diagnosis of SAS is made based on the pulse waves detected by the pulse sensor 1. As a result, SAS can be detected and treated at the earliest possible time.

What is claimed is:

1. A method for detecting a physiological condition of a patient comprising the steps of:
    emitting light into the body of the patient;
    detecting pulse waves from the body of the patient from light reflected by the body of the patient;
    creating an envelope of the pulse waves;
    analyzing the envelope; and
    determining whether the patient is in a specific physiological condition based on a result of the analysis.

2. A method for detecting a physiological condition of a patient as in claim 1,
    wherein the step of analyzing includes the step of:
    calculating for every regular time interval a statistical index which represents characteristics of the envelope over the time interval, and
    wherein the step of determining includes using the statistical index.

3. A method for detecting a physiological condition of a patient comprising:
    detecting pulse waves from the body of the patient;
    calculating a pulse height of each of the pulse waves;
    analyzing the pulse height; and
    determining whether the patient is in a specific physiological condition based on a result of the analysis,
    wherein the step of analyzing includes the step of:
    calculating for every regular time interval a statistical index which represents characteristics of the pulse height over the time interval, and
    wherein the step of determining includes using the statistical index.

4. A method for detecting a physiological condition of a patient comprising:
    detecting pulse waves from the body of the patient;
    calculating a pulse height of each of the pulse waves;
    analyzing the pulse height; and
    determining whether the patient is in a specific physiological condition based on a result of the analysis,
    wherein the step of analyzing includes the steps of:
    creating a baseline of the pulse waves by connecting middle points of the pulse height; and
    calculating for every regular time interval a statistical index which represents characteristics of the baseline over the time interval, and
    wherein the step of determining includes using the statistical index.

5. A method for detecting a sleep condition of a patient comprising the steps of:
    emitting light into the body of the patient;
    detecting pulse waves from the sleeping body of the patient from light reflected by the body of the patient;
    creating an envelope of the pulse waves by connecting one of tops and bottoms of the pulse waves;
    determining that the patient is in non-REM sleep if the envelope fluctuates regularly; and
    determining that the patient is in REM sleep if the envelope fluctuates irregularly.

6. A method for detecting a sleep condition of a patient as in claim 5, further comprising the step of:
    calculating for every regular time interval a statistical index which represents characteristics of the envelope over the time interval,
    wherein the steps of determining include using the statistical index.

7. A method for detecting a sleep condition of a patient as in claim 6,
    wherein the statistical index includes at least one of an average, a maximum value, a minimum value, a variance, a deviation of a level of the envelope.

8. A method for detecting a physiological condition of a patient as in claim 5,
    wherein the pulse waves are detected from one of the wrist and forearm of the patient.

9. A method for detecting a sleep condition of a patient comprising the steps of:

detecting pulse waves from the sleeping body of the patient;

calculating a pulse height of each of the pulse waves;

determining that the patient is in non-REM sleep if the pulse height fluctuates regularly; and determining that the patient is in REM sleep if the pulse height fluctuates irregularly.

10. A method for detecting a sleep condition of a patient as in claim 9, further comprising the step of:

calculating for every regular time interval a statistical index which represents characteristics of the pulse height over the time interval, wherein the steps of determining include using the statistical index.

11. A method for detecting a sleep condition of a patient as in claim 10, wherein the statistical index includes at least one of an average, a maximum value, a minimum value, a variance, a deviation of the pulse height.

12. A method for detecting a sleep condition of a patient as in claim 9, wherein the pulse waves are detected from one of the wrist and forearm of the patient.

13. A method for detecting a sleep condition of a patient comprising the steps of:

detecting pulse waves from the sleeping body of the patient;

calculating a pulse height of each of the pulse waves;

creating a baseline of the pulse waves by connecting middle points of the pulse height;

determining that the patient is in non-REM sleep if the baseline fluctuates regularly; and determining that the patient is in REM sleep if the baseline fluctuates irregularly.

14. A method for detecting a sleep condition of a patient as in claim 13, further comprising the step of:

calculating for every regular time interval a statistical index which represents characteristics of the baseline over the time interval, wherein the steps of determining include using the statistical index.

15. A method for detecting a sleep condition of a patient as in claim 14, wherein the statistical index includes at least one of an average, a maximum value, a minimum value, a variance, a deviation of a level of baseline.

16. A method for detecting a sleep condition of a patient as in claim 13, wherein the pulse waves are detected from one of the wrist and forearm of the patient.

17. A method for diagnosing whether a sleeping patient has sleep apnea syndrome comprising the steps of:

detecting pulse waves from the sleeping body of the patient;

analyzing the pulse waves; and determining whether the patient has sleep apnea syndrome based on a result of the analysis.

18. A method for diagnosing whether a sleeping patient has sleep apnea syndrome as in claim 17, further comprising the step of:

determining whether a type of the sleep apnea syndrome is obstructive sleep apnea based on the result of the analysis.

19. A method for diagnosing whether a sleeping patient has sleep apnea syndrome as in claim 18, wherein the step of analyzing creates an envelope of the pulse waves by connecting one of tops and bottoms of the pulse waves and calculates a degree of fluctuation of the envelope, and wherein the steps of determining indicate that the patient has obstructive sleep apnea syndrome if the degree of the fluctuation of the envelope exceeds a predetermined level.

20. A method for diagnosing whether a sleeping patient has sleep apnea syndrome as in claim 18, wherein the step of analyzing calculates a degree of fluctuation of peaks of the pulse waves, and wherein the steps of determining indicate that the patient has obstructive sleep apnea syndrome if the degree of the fluctuation of the peaks exceeds a predetermined level.

21. A method for diagnosing whether a sleeping patient has sleep apnea syndrome as in claim 18, wherein the step of analyzing calculates a pulse height of each of the pulse wave and a degree of fluctuation of the pulse height, and wherein the steps of determining indicate that the patient has obstructive sleep apnea syndrome if the degree of the fluctuation of the pulse height exceeds a predetermined level.

22. A method for diagnosing whether a sleeping patient has sleep apnea syndrome as in claim 18, wherein the step of analyzing calculates a pulse area which is defined by each of the pulse waves, and a degree of variation of the pulse area, and wherein the steps of determining indicate that the patient has obstructive sleep apnea syndrome if the degree of the variation of the pulse area exceeds a predetermined level.

23. A method for diagnosing whether a sleeping patient has sleep apnea syndrome as in claim 18, wherein the step of analyzing calculates a pulse length which is a length of each of the pulse waves, and a degree of variation of the pulse length, and wherein the steps of determining indicate that the patient has obstructive sleep apnea syndrome if the degree of the variation of the pulse length exceeds a predetermined level.

24. A method for diagnosing whether a sleeping patient has sleep apnea syndrome as in claim 18, wherein the steps of determining include using fluctuation of the pulse waves.

25. A method for diagnosing whether a sleeping patient has sleep apnea syndrome as in claim 24, wherein the step of analyzing calculates a difference between the fluctuation of the pulse waves and fluctuation of pulse waves detected from the patient in an eupneic condition, and wherein the steps of determining indicate that the patient has obstructive sleep apnea syndrome if the degree of the difference exceeds a predetermined level.

26. A method for diagnosing whether a sleeping patient has sleep apnea syndrome as in claim 18, wherein the step of analyzing creates a first envelope of the pulse wave which connects tops of the pulse waves and a second envelope of the pulse waves which connects bottoms of the pulse waves, wherein the step of analyzing further calculates a closeness of one of bottoms of the first envelope and corresponding one of tops of the second envelope, and wherein the steps of determining indicate that the patient has obstructive sleep apnea syndrome if the closeness exceeds a predetermined level.

27. A method for diagnosing whether a sleeping patient has sleep apnea syndrome as in claim 17, further comprising the step of:
   determining whether a type of the sleep apnea syndrome is central sleep apnea based on the result of the analysis.

28. A method for diagnosing whether a sleeping patient has sleep apnea syndrome as in claim 27,
   wherein the step of analyzing creates an envelope of the pulse waves by connecting one of tops and bottoms of the pulse waves, and calculates a period of fluctuation of the envelope, and
   wherein the steps of determining indicate that the patient has central sleep apnea syndrome if the period exceeds a predetermined length.

29. A method for diagnosing whether a sleeping patient has sleep apnea syndrome as in claim 17, further comprising the step of:
   determining whether a type of the sleep apnea syndrome is mixed sleep apnea.

30. A method for diagnosing whether a sleeping patient has sleep apnea syndrome as in claim 19,
   wherein the step of determining whether the patient has sleep apnea syndrome detects obstructive sleep apnea condition and central sleep apnea condition based on the result of analysis, and
   wherein the step of determining the type of the sleep apnea syndrome indicates that the patient has mixed sleep apnea syndrome if the obstructive sleep apnea condition is detected after the central sleep apnea condition is detected.

31. An apparatus for detecting a physiological condition of a patient comprising:
   a light emitter for emitting light into the body of the patient;
   a pulse sensor for detecting light reflected by the body of the patient and therefore detecting pulse waves from the body of the patient;
   a drive circuit for driving the pulse sensor;
   a data processing unit for executing a program for creating and analyzing an envelope of the pulse waves and detecting a physiological condition based on a result of the analysis; and
   a display unit for displaying a result of the detection.

32. An apparatus for detecting a physiological condition of a patient as in claim 31,
   wherein the pulse sensor is designed to be worn on one of the wrist and finger of the patient.

33. An apparatus for detecting a physiological condition of a patient as in claim 31,
   wherein the pulse waves are detected from the patient, and
   wherein the data processing unit executes the program for detecting a sleep condition of the patient based on the result of the analysis.

34. An apparatus for detecting a physiological condition of a sleeping patient comprising:
   a pulse sensor for detecting pulse waves from the patient body, wherein the pulse waves are detected from the sleeping patient;
   a drive circuit for driving the pulse sensor;
   a data processing unit for executing a program for creating and analyzing an envelope of the pulse waves and detecting a physiological condition based on a result of the analysis, wherein the data processing unit executes the program for detecting a respiratory condition of the patient based on the result of the analysis; and
   a display unit for displaying a result of the detection.

* * * * *